United States Patent [19]

Ono et al.

[11] Patent Number: 5,215,671
[45] Date of Patent: Jun. 1, 1993

[54] PURIFICATION METHOD OF 2-CHLOROPROPIONIC ACID

[75] Inventors: Yuzo Ono; Thutomu Kajikuri; Shoji Kitado; Kenji Senoo, all of Takaishi, Japan

[73] Assignee: Mitsui Toatsu Chemicals, Incorporated, Tokyo

[21] Appl. No.: 712,162

[22] Filed: Jun. 11, 1991

[30] Foreign Application Priority Data

Jun. 11, 1990 [JP] Japan .................................. 2-149961
Jun. 11, 1990 [JP] Japan .................................. 2-149962

[51] Int. Cl.$^5$ .......................... B01D 3/00; B01D 1/00
[52] U.S. Cl. ...................................... 210/774; 203/89; 210/758; 210/761; 210/762; 210/763; 210/767; 562/531; 562/602; 562/603
[58] Field of Search ............... 210/681, 684, 688, 754, 210/758, 761, 762, 759, 760, 763, 774, 767; 203/89; 562/602, 603, 531

[56] References Cited

U.S. PATENT DOCUMENTS

| | | | |
|---|---|---|---|
| 1,993,713 | 3/1935 | Bass et al. | 562/603 |
| 2,010,685 | 6/1935 | Bass et al. | 562/603 |
| 2,379,759 | 7/1945 | Spence et al. | 562/602 |
| 2,930,801 | 3/1960 | Montagna et al. | 562/531 |
| 2,959,613 | 11/1960 | Whitfield | 562/531 |
| 3,584,036 | 6/1971 | Sexton et al. | 562/603 |
| 3,671,584 | 6/1972 | Schlect et al. | 562/603 |
| 3,772,157 | 11/1973 | Horsley | 203/56 |
| 4,487,720 | 12/1984 | Fruchey | 562/531 |
| 4,812,203 | 3/1989 | Obata et al. | 203/89 |
| 4,944,839 | 7/1990 | Rosenblad | 203/89 |

FOREIGN PATENT DOCUMENTS

| | | |
|---|---|---|
| 2582645 | 12/1986 | France . |
| 50-58014 | 5/1975 | Japan . |
| 61-126046 | 6/1986 | Japan . |
| 62-96446 | 5/1987 | Japan . |
| 448145 | 6/1936 | United Kingdom . |

*Primary Examiner*—Robert A. Dawson
*Assistant Examiner*—Sun Uk Kim
*Attorney, Agent, or Firm*—Cushman, Darby and Cushman

[57] ABSTRACT

The present invention is directed to a method for recovering 2-chloropropionic acid so that this compound can be separated in a high-purity form. According to the method, crude 2-chloropropionic acid is heat-treated in the presence of a metal compound at a temperature in the range of 130°–180° C. where dichloro derivatives are contained as impurities or at a temperature not exceeding 160° C. where no dichloro derivatives are contained. The metal compound is then removed at 160° C. or lower. Final purification is thereafter conducted to obtain 2-chloropropionic acid as a high-purity product.

20 Claims, No Drawings

PURIFICATION METHOD OF 2-CHLOROPROPIONIC ACID

BACKGROUND OF THE INVENTION

1. Field of the Invention

The present invention relates to a method for recovering 2-chloropropionic acid (hereinafter called "α-CPA") with high purity from crude α-CPA or a crude α-CPA-containing solution.

2. Description of the Related Art

α-CPA is used as an intermediate for various chemical products such as lactic acid and alanine, agricultural chemicals, pharmaceuticals, etc. In recent years, there is a growing demand for its high purity product in the field of a racemic resolution.

α-CPA is produced by chlorination of propionic acid industrially. Its production is conducted in accordance with the following reaction formula:

$$CH_3CH_2COOH + Cl_2 \rightarrow CH_3CHClCOOH + HCl \quad (1)$$

As impurities, more chlorinated dichloro derivatives such as 2,2-dichloropropionic acid are generally contained on the order of several percents in addition to unreacted propionic acid. Moreover, it has heretofore been considered difficult to produce a high-purity product of 99 wt. % or higher by conventional methods. The term "dichloro derivatives" as used herein means chlorinated compounds of propionic acid, in which two hydrogen atoms have been substituted by the like number of chlorine atoms. In general, 2,2-dichloropropionic acid is a predominant component of the dichloro derivatives. The boiling points of these dichloro derivatives are extremely close to that of α-CPA so that they can hardly be separated out by conventional distillation. As a matter of fact, none of the other separation methods have been found acceptable from the industrial standpoint.

For these reasons, the purity is around 98–99 wt. % even in the case of α-CPA currently produced as a high-purity product in the industry. α-CPA whose purity is 99 wt. % or higher is not produced by the chlorination of propionic acid.

Recently, a process has been proposed for the production of α-CPA whose purity is as high as 99 wt. % or more (Japanese Patent Laid-Open No. 96446/1987). This process features oxidation of 2-chloropropionaldehyde (hereinafter called "α-CPL") with oxygen or an oxygen-containing gas in a liquid phase in the presence of a metal compound catalyst.

The production process of α-CPA by liquid-phase oxidation of α-CPL proceeds in accordance with the following reaction formula:

$$CH_3CHClCHO + \tfrac{1}{2}O_2 \rightarrow CH_3CHClCOOH \quad (2)$$

The starting material, α-CPL, can be produced by the reaction of vinyl chloride and synthesis gas in the presence of rhodium and a base, for example, as disclosed in Japanese Patent Laid-Open No. 126046/1986. Accordingly, chlorine is not used and almost no byproduction of hardly-separable dichloro derivatives takes place, thereby making it possible to produce high-purity α-CPA of 99 wt. % or more.

For the removal of dichloro derivatives, Japanese Patent Laid-Open No. 58014/1975 discloses an azeotropic distillation method which makes use of an aliphatic hydrocarbon as an azeotrope former. Even in this process, the difference in boiling point between the azeotropic mixture of the azeotrope former so added and α-CPA and the azeotropic mixture of the thus-added azeotrope former and each dichloro derivative is however not substantially large. Production of high-purity α-CPA therefore requires not only a distillation column having an extremely large number of plates or trays and requiring huge energy but also an additional step for the separation and recovery of the azeotrope former.

French Patent 2582645 discloses a method in which hydrogenation is conducted in the presence of a metal catalyst such as palladium, rhodium or ruthenium to convert hardly-separable dichloro derivatives to propionic acid having the lower boiling point, followed by distillation for purification. This method however requires hydrogen. Moreover, hydrogen chloride is byproduced together with propionic acid, thereby making the method unfavorable from the viewpoint of protection of the production facilities from corrosion.

On the other hand, in the production process of high-purity α-CPA by liquid-phase oxidation of α-CPL, the reaction mixture contains unreacted α-CPL, reaction byproducts, a catalyst, a solvent, and so on. Purification by conventional distillation however leads to problems such that α-CPA cannot be obtained in a colorless, clear form probably due to its poor thermal stability and α-CPA is lost substantially by modification during the purification.

SUMMARY OF THE INVENTION

An object of the present invention is to overcome various problems in the purification of α-CPA, such as those mentioned above, and to provide a purification method for obtaining high-purity α-CPA by a simple operation.

The present inventors have proceeded with an extensive investigation to achieve the above object, leading to the completion of the present invention.

The present invention therefore provides a method for recovering α-CPA with high purity from a crude α-CPA solution containing a metal compound. The method comprises finally purifying and recovering α-CPA subsequent to removal of the metal compound at a temperature not higher than 160° C.

Purification of α-CPA by the method of this invention makes it possible to industrially obtain, in a high yield, high-purity α-CPA of 99 wt. % or more which has not been available to date.

DETAILED DESCRIPTION OF THE INVENTION

The term "crude α-CPA-containing solution" as used herein means α-CPA or a solution containing α-CPA, which has been obtained after chlorination of propionic acid and contains chlorinated derivatives of propionic acid, each of said derivatives containing two chlorine atoms substituted for the like number of hydrogen atoms. As an alternative, it also means a reaction mixture obtained by liquid-phase oxidation of α-CPL with oxygen or an oxygen-containing gas. In the former case, heating is conducted after addition of a metal compound. In the latter case, the reaction mixture is added with a metal compound as a catalyst for the liquid-phase oxidation, is oxidized under heat and pressure, and then is concentrated or preliminarily purified.

In the case of the former crude α-CPA solution, modification of dichloro derivatives proceed further as the temperature of the heat treatment becomes higher. An unduly high temperature however leads to modification of α-CPA itself. On the other hand, an excessively low temperature results in a reduction in the efficiency of the modification of the dichloro derivatives. The temperature of the heat treatment may therefore be at least 110° C., preferably 130°–180° C. The time of the heat treatment can be determined as needed because it varies depending on the amount of the metal compound and also the temperature of the heat treatment. In practice, the most economical conditions are adopted in view of the initial cost, the purity of α-CPA required as a final product, the loss of α-CPA in the course of purification, etc.

α-CPA or α-CPA-containing solution, which has been obtained by oxidation of α-CPL is basically almost free of dichloro derivatives. It has been confirmed by gas chromatographic analysis that the total content of unidentified impurities relatively close in boiling point to α-CPA is significantly reduced by a series of heat treatment operations although the total content of unidentified impurities having higher boiling points is slightly increased by these heat treatment.

The purification operation includes the separation and removal of various low boiling-point substances, the recovery of a solvent, the removal of the metal compound, the removal of high boiling-point substances, and the like. It is common to conduct the distillation in such a way that these substances are successively separated out in an increasing order of boiling point. The oxidation reaction of α-CPL is generally subjected in the absence or presence of solvent which includes carboxylic acid such as acetic acid, propionic acid and lactic acid, dimethyl sulfoxide, sulfolane and acetone. Moreover, α-CPA which is a product can also be used as solvent. In the case of a reaction mixture obtained by liquid-phase oxidation of α-CPL, said reaction mixture being substantially free of dichloro derivatives, α-CPA so produced is kept heated in the presence of a metal compound until the final purification stage. Heating in the presence of such a metal compound promotes dechlorination of α-CPA and conversion of α-CPA to substances having higher boiling points. Although this tendency is observed at temperatures as low as about 100° C., it generally becomes prominent at 130° C. and higher, especially at high temperatures over 150° C. A reaction mixture obtained after such a heating operation therefore tends to show an abrupt increase of propionic acid, coloration in a dark brown color, etc. Coloration in a pale yellow or purple color is also observed on purified α-CPA so that no colorless, clear product is available.

Although it is not considered preferable to heat the reaction mixture for a long time at 130° C. or higher, especially at a high temperature over 150° C. in the presence of the metal compound employed in the oxidation reaction, this heating operation does not give any substantial influence provided that it is carried out only for a short period. Accordingly, the preferred heating time is generally within 1 hour in total over the range of 130°–150° C. although it depends to large extent upon the temperature and the amount of the metal compound. It is highly recommended to avoid heating at 150° C. and higher, especially at temperatures over 160° C. because heating at such high temperatures leads to an abrupt increase of propionic acid and also to coloration of the reaction mixture in a dark brown color.

As has been described above, the heating operation in the presence of the metal compound leads to an increase in the purification loss of α-CPA and also to coloration of distilled α-CPA, thereby failing to obtain the desired, colorless, clear product. In other words, if the final purification, i.e., distillation operation is conducted without removal of the metal compound, coloration of distilled α-CPA in a yellow or purple color is observed not only at high temperatures but also temperatures of 130° C. and lower so that no colorless, clear distillate can be obtained.

The method of the present invention therefore has made it possible to produce high-purity, colorless, clear α-CPA owing to the removal of the metal compound at least prior to the final purification of α-CPA. In the case of an α-CPA-containing solution substantially free of dichloro derivatives, the loss of α-CPA by modification during its purification can be reduced by controlling the maximum heating temperature in the presence of the metal compound at a level not higher than 160° C., preferably at 150° C. or lower.

Regarding the separation of the metal compound, it is only necessary to conduct the separation before the maximum temperature reaches 160° C., preferably 150° C. The metal compound may therefore be separated out directly from the reaction mixture. In practice, a most economical method is however adopted in view of the quantity of energy to be required, the loss of α-CPA due to modification, the initial cost and the like. For example, when the oxidation reaction is conducted in acetic acid as a solvent and α-CPA is then purified by distillation, it is desirable to conduct the removal of the metal compound subsequent to separation and recovery of the solvent and then to conduct high-level purification of α-CPA because the boiling point of acetic acid is lower than α-CPA and separation of the metal compound in an earlier stage requires evaporation of acetic acid, which is used in a large quantity, twice and hence makes the purification method un economical in both energy and initial cost. The separation of the metal compound can be effected, for example, by an evaporation method—which makes use of a falling-film evaporator and features a short contact time and no substantial temperature increase as the solution is subjected to evaporation in the form of a thin layer—or by an extraction method applied at temperatures not higher than 150° C.

The metal compound usable in the present invention is at least one metal compound selected from the group consisting of iron compounds, cobalt compounds, nickel compounds, manganese compounds, copper compounds, cerium compounds and molybdenum compounds. The metal compound is often used in the form of a soluble salt such as a mineral acid salt or a carboxylate salt.

More specifically, preferred iron compounds include mineral acid salts of iron(II) or (III), such as ferrous chloride, ferric chloride, ferrous sulfate, ferric sulfate, ferrous nitrate and ferric nitrate; and iron(II) or (III) carboxylates such as ferrous acetate, ferric acetate, ferrous benzoate and ferric oxalate. In addition, the iron salt of α-CPA is also used frequently. Besides, ferric hydroxide and ferric oxide can also be used.

Preferred cobalt compounds include mineral acid salts of cobalt, such as cobalt chloride, cobalt sulfate and cobalt nitrate; and cobalt carboxylates such as cobalt acetate, cobalt formate, cobalt oxalate and cobalt naphthenate. The cobalt salt of α-CPA is also used frequently. In addition, cobalt hydroxide, cobalt oxide and basic cobalt carbonate can also be used.

Preferred nickel compounds include mineral acid salts of nickel, such as nickel chloride, nickel bromide, nickel iodide, nickel sulfate and nickel nitrate; and nickel carboxylates such as nickel acetate, nickel formate, nickel oxalate and nickel benzoate. The nickel salt of α-CPA is also used frequently. Besides, nickel carbonate, nickel hydroxide, nickel oxide and the like can also be used.

Preferred manganese compounds include mineral acid salts of manganese, such as manganese chloride, manganese sulfate and manganese nitrate; and manganese carboxylates such as manganese acetate, manganese formate, manganese benzoate and manganese naphthenate. In addition, the manganese salt of α-CPA is also used frequently. Besides, manganese dioxide, manganese carbonate and the like can also be used.

Preferred copper compounds include mineral acid salts of Cu(I) or (II), such as cuprous chloride, cupric chloride, copper sulfate and copper nitrate; and copper-(II) carboxylates such as cupric acetate, cupric formate, cupric citrate and cupric naphthenate. In addition, the copper salt of α-CPA is also used frequently. Besides, cuprous oxide, cupric oxide, cupric hydroxide, copper carbonate and the like can also be used.

Preferred cerium compounds include mineral acid salts of cerium(III) or (IV), such as cerous chloride, cerous sulfate, ceric sulfate and cerous nitrate; and cerium(III) or (IV) carboxylates such as cerous acetate ceric acetate. In addition, the cerium salt of α-CPA is also often used. Besides, ceric oxide, cerous carbonate and the like can also be used.

Preferred molybdenum compounds include mineral acid salts of molybdenum(II), (III) or (V), such as molybdenum dichloride, molybdenum trichloride and molybdenum pentachloride; and molybdenum(V) carboxylates such as molybdenum acetate and molybdenum o naphthenate. In addition, the molybdenum salt of α-CPA is also used frequently.

Two or more of these metal compounds can be used in combination, to say nothing of their single use. Although no particular limitation is imposed on the amount to be used, the greater the better in view of the efficiency of modification of dichloro derivatives. In view of the handling and economy, it is generally desirable to use the metal compound in an amount such that the metal is contained in the range of from 0.01 wt. % to 10 wt. % based on α-CPA.

By the operation as described above, dichloro derivatives whose removal is difficult are modified and converted to low boiling-point substances, such as propionic acid or acetic acid, and high boiling-point substances—both of which can be easily separated out by distillation—and are also modified to α-CPA itself. It has also been confirmed that impurities, whose boiling points are close to one of α-CPA, other than such dichloro derivatives are also lowered in content along the passage of time by the above treatment. Therefore, after the above heat treatment has been applied, the total content of impurities such as dichloro derivatives is much lower compared to their total content before the treatment and, further, the yield of α-CPA is improved.

α-CPA or an α-CPA-containing solution obtained as described above is purified by distillation or the like, whereby high-purity α-CPA is produced. In this case, the substances to be removed have been changed by the heat treatment from dichloro derivatives having boiling points extremely close to α-CPA to substances whose boiling points are substantially different from the boiling point of α-CPA, such as propionic acid, acetic acid and high boiling-point substances. α-CPA can therefore be easily purified by conventional distillation. Although no particular limitation is imposed on the conditions for the distillation, the number of theoretical plates may be from about 3 to about 20 and a reflux ratio of 0.1–3 or so is sufficient. Even by such a simple, conventional distillation, i.e., purification operation that does not involve addition of an azeotrope former as described above, high-purity α-CPA which has not been available to date can still be produced.

The present invention will hereinafter be described specifically by the following examples, which are presented to illustrate a few embodiments of the invention and shall not be taken as limiting the scope of the present invention.

EXAMPLE 1

Synthesis of α-CPA

α-CPL (85 wt. %) was dissolved in acetic acid to provide a 10 wt. % α-CPL solution. In the solution, cobalt acetate and the iron salt of α-CPA were dissolved at concentrations of 4 ppm and 40 ppm by weight in terms of the metals, respectively. The resultant solution was continuously fed to a 1-l autoclave equipped with a stirrer, in which an air-induced oxidation reaction was conducted at 50° C. and 80 kg/cm$^2$ G. The reaction mixture thus obtained contained, besides acetic acid, 6 wt. % of α-CPA, 5 wt. % of α-CPL, 2 wt. % of water, and small amounts of low boiling-point impurities and high boiling point impurities such as the catalysts.

Separation of Low Boiling-Point Substances

The reaction mixture was processed in a 10-l rotary evaporator so that 85% of the acetic acid was evaporated. The final oil bath temperature was 84° C.

Distillation, namely, purification of the resultant concentrate was next continuously conducted in a glass-made, 40-plate Oldershaw distillation column, whereby low boiling-point substances such as still remaining acetic acid and water were removed. At that time, the temperature of the bottom and the average residence time were 124° C. and 6 hours respectively, and the bottom had a dark brown color. In addition, the concentrations of propionic acid in the distillate and bottom were 2.2 times and 1.4 times as much as that in the feed, respectively. It was hence confirmed that the concentration of propionic acid increased by the heating applied during the distillation.

Separation of Catalysts and Final Purification

The bottom was continuously fed to a falling-film evaporator equipped with a stirrer, whereby separation of the catalysts was conducted. The highest temperature which the heating medium reached was 160° C. and the distillate was tinged in a yellow color. Subsequently, the distillate was processed batchwise in the abovedescribed Oldershaw distillation column to conduct high-level purification of α-CPA. The bottom temperature was 125° C. initially but arose to 150° C. finally. The reflux ratio was in the range of 0.5–1.5. After initial distillate fractions were distilled out to the total amount of 10 wt. %, the receiver was replaced by a new one and α-CPA was continuously distilled. As a result, a colorless, clear distillate was obtained. The distillate so obtained was analyzed by gas chromatography. It was confirmed that high-purity α-CPA of 99.6 wt. % was obtained.

EXAMPLE 2

Purification of α-CPA was conducted in a similar manner to Example 1 except that continuous separation of the catalysts was conducted directly from a reaction mixture in the stirrer-equipped, falling-film evaporator.

The degree of coloration of a bottom obtained upon removal of low boiling-point substances in the Oldershaw distillation column was much lower than that of the bottom in Example 1. By the heating applied during the distillation, propionic acid was produced only in an extremely small amount. Further, substantially no propionic acid was detected in the bottom. In the final purification by batchwise distillation, a colorless, clear distillate was obtained after initial distillate fractions in the total amount of only 5 wt. % were distilled out, and its purity was as high as 99.7 wt. %.

COMPARATIVE EXAMPLE 1

Purification of α-CPA was conducted in a similar manner to Example 1 except that the separation of the catalysts was not conducted. In the final purification by distillation, initial distillate fractions in the total amount of 10 wt. % were distilled out at the reflux ratio of 0.5. The distillate however showed a pale purple color and its purity was as low as 99.0 wt. %. The reflux ratio was then increased to 2.0, at which distillation was continuously conducted until the total amount of the distillate reached 40 wt. %. The distillate still had a color although the degree of coloration had been reduced a little. Further, the purity was 99.4 wt. %, which was lower than the value obtained in Example 1.

EXAMPLE 3

In a 50-ml glass vessel, were placed and sealed 0.06 g of cobalt acetate, 0.6 g of the iron salt of α-CPA, and 30 g of α-CPA containing 3.3 wt. % of dichloro derivatives. The vessel was placed in a silicone oil bath heated at 150° C. and was subjected to heat treatment for a predetermined time.

As a result, as is shown in Table 1, it was confirmed that the total content of dichloro derivatives decreased and the total content of low boiling-point impurities composed principally of propionic acid and acetic acid and the total content of the non-volatile residue both increased and also that the content of α-CPA increased slightly. As is appreciated from the table, compared to the total content of dichloro derivatives before the heat treatment, the total content decreased close to about a quarter after 5 hours of the heat treatment and dropped to one tenths or lower after 10 hours of the heat treatment.

EXAMPLE 4

Heat treatment of an α-CPA mixture having the same composition as that treated in Example 3 was conducted in a similar manner to Example 3 except that the temperature of the silicone oil bath was lowered to 130° C. The results are shown in Table 1.

As is understood from Table 1, it was confirmed similarly to Example 3 that the total content of dichloro derivatives decreased and the total content of low boiling-point impurities composed principally of propionic acid and acetic acid and the total content of the non-volatile residue both increased and also that the content of α-CPA increased slightly. After 10 hours of the heat treatment, the total content of dichloro derivatives dropped to a half or less.

EXAMPLE 5

In a 1-l glass flask fitted with a stirrer and condenser, were placed 700 g of α-CPA mixture having the same composition as that employed in Example 3, 1.4 g of cobalt acetate and 14 g of the iron salt of α-CPA, followed by heat treatment for 5 hours in an oil bath of 150° C. The content of dichloro derivatives after the heat treatment significantly dropped to 0.8 wt. %.

In a glass-made, falling-film evaporator, the catalysts were removed at 160° C. from the α-CPA mixture so heat-treated. The crude α-CPA was then distilled and purified in an Oldershaw distillation column whose practical plate number was 10. The distillation was conducted batchwise at the reflux ratio of 1. After 5 wt. % of distillate was driven out as initial distillate fractions, the distillate receiver was replaced by a new one and the distillate was collected within the range of distillation percentages of 5–90%. An analysis of the composition of the distillate was performed by gas chromatography. The purity of α-CPA was found to be 99.5 wt. %, which was extremely high purity.

COMPARATIVE EXAMPLE 2

Heat treatment of α-CPA was conducted in a similar manner to Example 3 except that the metal compounds were not added.

As is seen from Table 2, substantially no decrease was observed in the total content of dichloro derivatives even after 10 hours of heat treatment.

COMPARATIVE EXAMPLE 3

Heat treatment of α-CPA was conducted in a similar manner to Example 3 except that the temperature of the heat treatment was lowered to 100° C.

As is envisaged from Table 2, substantially no decrease was observed in the total content of dichloro derivatives even after 10 hours of heat treatment.

TABLE 1

| Heating time (hr) | | 1.0 | 2.0 | 5.0 | 10.0 |
|---|---|---|---|---|---|
| Ex. 3 | α-CPA | 94.7 | 95.5 | 96.0 | 96.4 |
| | Dichloro derivatives | 3.3 | 2.2 | 0.9 | 0.3 |
| | PrOH + AcOH | 0.2 | 0.4 | 0.7 | 0.8 |
| | Non-volatile residue | 1.1 | 1.6 | 2.3 | 2.5 |
| Ex. 4 | α-CPA | 94.7 | 95.0 | 95.5 | 96.0 |
| | Dichloro derivatives | 3.3 | 2.9 | 2.1 | 1.5 |
| | PrOH + AcOH | 0.2 | 0.3 | 0.4 | 0.5 |
| | Non-volatile residue | 1.1 | 1.3 | 1.5 | 1.6 |

(Note)
PrOH + AcOH: The total content of propionic acid and acetic acid.
Unit: wt. %.

TABLE 2

| Heating time (hr) | | 1.0 | 2.0 | 5.0 | 10.0 |
|---|---|---|---|---|---|
| Comp. Ex. 2 | α-CPA | 96.0 | 96.0 | 96.0 | 95.9 |
| | Dichloro derivatives | 3.3 | 3.3 | 3.2 | 3.2 |
| | PrOH + AcOH | 0.2 | 0.2 | 0.2 | 0.2 |
| | Non-volatile residue | 0 | 0 | 0 | 0.1 |
| Comp. Ex. 3 | α-CPA | 94.7 | 94.7 | 94.8 | 94.9 |
| | Dichloro derivatives | 3.3 | 3.3 | 3.2 | 3.0 |
| | PrOH + AcOH | 0.2 | 0.2 | 0.2 | 0.3 |
| | Non-volatile residue | 1.1 | 1.1 | 1.2 | 1.2 |

We claim:

1. A method of recovering 2-chloropropionic acid with high purity from a crude 2-chloropropionic acid solution containing a metal compound, which comprises highly purifying and recovering 2-chloropropionic acid to achieve a product purity of at least 99 Wt. % by distillation subsequent to removal of the metal compound at a temperature not higher than 160° C. by evaporation or extraction to prevent deterioration of said 2-chloropropionic acid.

2. The method of claim 1, wherein the crude 2-chloropropionic acid solution has been obtained by subjecting 2-chloropropionaldehyde to liquid-phase oxidation with oxygen or an oxygen-containing gas in the presence of the metal compound; and the crude 2-chloropropionic acid solution is subjected to removal of compounds selected from the group consisting of solvent, unreacted aldehyde and byproducts of the reaction under temperature conditions not exceeding 160° C. at the maximum to prevent deterioration of 2-chloropropionic acid prior to the removal of the metal compound.

3. The method of claim 2, wherein the metal compound is at least one metal compound selected from the group consisting of iron compounds, cobalt compounds, nickel compounds, manganese compounds, copper compounds, cerium compounds and molybdenum compounds.

4. The method of claim 3, wherein the metal compound is a soluble metal salt.

5. The method of claim 4, wherein the soluble metal salt is at least one metal salt selected from the group consisting of metal acetates, metal naphthenates and metal 2-chloropropionates.

6. The method of claim 2, wherein the removal of compounds selected from the group consisting of solvent, unreacted aldehyde and byproducts of the reaction is conducted at a temperature not higher than 150° C.

7. The method of claim 2, wherein the removal of compounds selected from the group consisting of solvent, unreacted aldehyde and byproducts of the reaction is conducted at a temperature not higher than 130° C.

8. The method of claim 2, wherein the removal of compounds selected from the group consisting of a solvent, unreacted aldehyde and byproducts of the reaction is conducted within the temperature range of 130°–140° C. for a period not longer than 1 hour.

9. The method of claim 2, wherein the metal compound was used in an amount such that the metal is contained in the range of from 0.01 to 10 wt. % based on 2-chloropropionic acid.

10. The method of claim 2, wherein the separation and removal of the metal compound is conducted by falling-film evaporation.

11. The method of claim 1, wherein the separation and removal of the metal compound is conducted by extraction at a temperature not higher than 150° C.

12. A method for recovering 2-chloropropionic acid with high purity from crude 2-chloropropionic acid or a crude 2-chloropropionic acid containing solution containing a metal compound, which comprises highly purifying and recovering 2-chloropropionic acid to achieve a product purity of at least 99 Wt. % by distillation subsequent to removal of the metal compound at a temperature not higher than 160° C. by evaporation or extraction to prevent deterioration of said 2-chloropropionic acid, wherein said crude 2-chloropropionic acid or a crude 2-chloropropionic acid containing solution comprises as an impurity a chlorinated propionic acid derivative obtained by chlorinating propionic acid and having two chlorine atoms substituted for hydrogen atoms and wherein said crude 2-chloropropionic acid containing solution is heated in the presence of the metal compound.

13. The method of claim 12, wherein the metal compound is at least one metal compound selected from the group consisting of iron compounds, cobalt compounds, nickel compounds, manganese compounds, copper compounds, cerium compounds and molybdenum compounds.

14. The method of claim 13, wherein the metal compound is a soluble metal salt.

15. The method of claim 14, wherein the soluble metal salt is at least one metal salt selected from the group consisting of metal acetates, metal naphthenates and metal 2-chloropropionates.

16. The method of claim 12, wherein the heat treatment is conducted at a temperature not lower than 110° C.

17. The method of claim 12, wherein the heat treatment is conducted at a temperature in the range of 130°–180° C.

18. The method of claim 12, wherein the separation and removal of the metal compound is conducted by falling-film evaporation.

19. The method of claim 12, wherein the separation and removal of the metal compound is conducted by extraction at a temperature not higher than 150° C.

20. The method of claim 12, wherein the metal compound was used in an amount such that the metal is contained in the range of from 0.01 to 10 wt. % based on 2-chloropropionic acid.

* * * * *